US012754117B2

(12) United States Patent
Oki et al.

(10) Patent No.: US 12,754,117 B2
(45) Date of Patent: Oct. 6, 2026

(54) CORROSION ESTIMATION METHOD AND DEVICE

(71) Applicant: NTT, Inc., Tokyo (JP)

(72) Inventors: Shota Oki, Tokyo (JP); Shingo Mineta, Tokyo (JP); Mamoru Mizunuma, Tokyo (JP); Masayuki Tsuda, Tokyo (JP)

(73) Assignee: NTT, INC., Tokyo (JP)

( * ) Notice: Subject to any disclaimer, the term of this patent is extended or adjusted under 35 U.S.C. 154(b) by 266 days.

(21) Appl. No.: 18/690,136

(22) PCT Filed: Oct. 25, 2021

(86) PCT No.: PCT/JP2021/039232

§ 371 (c)(1),
(2) Date: Mar. 7, 2024

(87) PCT Pub. No.: WO2023/073751

PCT Pub. Date: May 4, 2023

(65) Prior Publication Data

US 2025/0130151 A1 Apr. 24, 2025

(51) Int. Cl.
*G01N 15/0205* (2024.01)
*G01N 15/00* (2024.01)
(Continued)

(52) U.S. Cl.
CPC ..... *G01N 15/0211* (2013.01); *G01N 15/0272* (2013.01); *G01N 15/04* (2013.01);
(Continued)

(58) Field of Classification Search
CPC ........... G01N 15/0211; G01N 15/0272; G01N 15/04; G01N 17/00; G01N 27/26; G01N 33/24; G01N 2015/0042
See application file for complete search history.

(56) References Cited

U.S. PATENT DOCUMENTS 12,140,527 B2 * 11/2024 Oki ........................ G01N 27/26
12,235,204 B2 * 2/2025 Oki ........................ G01N 17/02
(Continued)

FOREIGN PATENT DOCUMENTS

WO 2021100196 A1 5/2021

OTHER PUBLICATIONS

"Corrosive Soils: Causes, Effects, and Mitigation"; Testing Engineers; published Oct. 30, 2009; https://web.archive.org/web/20091030165759/https://www.testing-engineers.com/case1.html (Year: 2009).*
(Continued)

*Primary Examiner* — Ryan D Walsh
(74) *Attorney, Agent, or Firm* — Slater Matsil, LLP

(57) ABSTRACT

A particle size of soil is measured, a color measurement value related to a color of the soil is measured, and corrosion of a steel material buried in the soil is estimated from the particle size and the color measurement value. In the measurement of the color measurement value, a color value is measured as the color measurement value. In the corrosion estimation, a corrosion rate is obtained from the measured particle size, a corrosion rate magnification is obtained from the measured color measurement value, a corrected corrosion rate is obtained by multiplying the corrosion rate by the corrosion rate magnification, and the corrosion of the steel material is estimated according to the obtained corrected corrosion rate.

18 Claims, 10 Drawing Sheets

(51) Int. Cl.

| | |
|---|---|
| ***G01N 15/02*** | (2024.01) |
| ***G01N 15/04*** | (2006.01) |
| ***G01N 17/00*** | (2006.01) |
| ***G01N 27/26*** | (2006.01) |
| ***G01N 33/24*** | (2006.01) |

(52) U.S. Cl.
CPC ............. *G01N 17/00* (2013.01); *G01N 27/26* (2013.01); *G01N 33/24* (2013.01); *G01N 2015/0042* (2013.01)

(56) References Cited

U.S. PATENT DOCUMENTS

2022/0221387 A1* 7/2022 Oki ........................ G01N 33/24
2022/0414486 A1 12/2022 Mineta et al.
2025/0314579 A1* 10/2025 Oki ........................ G01N 17/00

OTHER PUBLICATIONS

Yan et al., "Corrosion Behaviors of Q235 Steel in Indoor Soil," International Journal of Electrochemical Science, 8 Oct. 20, 2013, 12531-12542. As discussed in the specification.

* cited by examiner

CORROSION ESTIMATION METHOD AND DEVICE

CROSS-REFERENCE TO RELATED APPLICATIONS

This application is a national phase entry of PCT Application No. PCT/JP2021/039232, filed on Oct. 25, 2021, which application is hereby incorporated herein by reference.

TECHNICAL FIELD

The present invention relates to a corrosion estimation method and a corrosion estimation device for estimating corrosion of a structure buried in soil.

BACKGROUND

To prevent failure of aged infrastructure facilities, maintenance operation by periodic inspection has been conventionally performed. However, visual inspection is difficult depending on installation places of facilities, and further, other appropriate inspection means as an alternative are not established in many cases. For this reason, for facilities for which inspection is difficult or impossible, an operation of uniformly updating facilities after a certain number of years, that is, a form of time-based maintenance has to be adopted.

To achieve both safety and efficiency of facilities for which the visual inspection is difficult, research and development of techniques for realizing condition-based maintenance by predicting and estimating a deterioration state of facilities has been actively conducted in recent years. If the condition-based maintenance can be realized, safety is secured by updating a target with fast deterioration progression without missing the target, and efficiency in terms of cost is expected to be improved by using a target with slow deterioration progression for a longer time.

CITATION LIST

Non Patent Literature

Non Patent Literature 1: Y. Wan et al., “Corrosion Behaviors of Q235 Steel in Indoor Soil”, International Journal of Electrochemical Science, vol. 8, pp. 12531-12542, 2013.

SUMMARY

Technical Problem

A typical example of the facilities for which the visual inspection is difficult is an underground facility. To predict soil corrosion that is a main cause of deterioration of metal materials buried in the ground, it is necessary to extract dominant environmental factors and grasp the degree of influence thereof. It is known that the soil corrosion proceeds on the basis of an oxidation-reduction reaction between water and oxygen, similarly to aqueous solution corrosion. However, unlike the aqueous solution corrosion, soil is a special environment in which three phases of a solid phase, a gas phase, and a liquid phase coexist, and there is a plurality of environmental factors related to the progress of soil corrosion, and therefore the soil corrosion is said to be a particularly complicated system (Non Patent Literature 1).

As described above, there is a problem that it is not easy to estimate the corrosion of the metal materials buried in the ground.

Embodiments of the present invention have been made to solve the above problem, and an object thereof is to easily estimate corrosion of a metal material buried in the ground.

Solution to Problem

A corrosion estimation method according to embodiments of the present invention includes a particle size measurement step of measuring a particle size of soil; a color measurement step of measuring a color measurement value related to a color of the soil; and an estimation step of estimating corrosion of a steel material buried in the soil from the particle size and the color measurement value.

Further, a corrosion estimation device according to embodiments of the present invention includes a particle size measuring instrument configured to measure a particle size of soil; a color measuring instrument configured to measure a color measurement value related to a color of the soil; and an estimation circuit configured to estimate corrosion of a steel material buried in the soil from the particle size and the color measurement value.

Advantageous Effects of Embodiments of Invention

As described above, according to embodiments of the present invention, since the corrosion of the steel material buried in the soil is estimated from the measured particle size and color measurement value, the corrosion of a metal material buried in the ground can be easily estimated.

DETAILED DESCRIPTION OF ILLUSTRATIVE EMBODIMENTS

Figure 1:
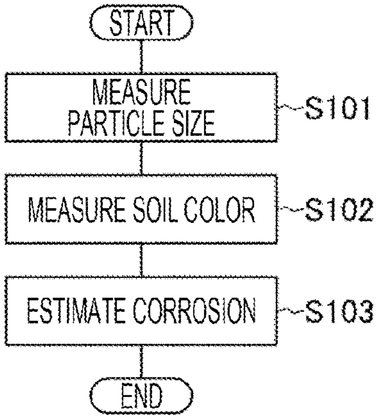
FIG. 1 is a flowchart for describing a corrosion estimation method according to an embodiment of the present invention.

Hereinafter, a corrosion estimation method according to an embodiment of the present invention will be described with reference to FIG. 1. In this method, first, in step S101, a particle size of soil is measured (particle size measurement step). For the measurement of the particle size, for example, JIS A 1204:2009 "The method for particle size distribution of soils" can be used. Further, a method conforming to JIS Z 8825:2013 "Particle size analysis-Laser diffraction methods" can be used.

Next, in step S102, a color measurement value related to a color of the soil is measured (color measurement step). In the measurement of the color measurement value, a color value can be measured as the color measurement value. In the measurement of the color measurement value, for example, a standard soil color chart in which standard soil colors are arranged by a Munsell system classification method can be used. In addition, a spectrophotometer can be used to measure the color measurement value.

Next, in step S103, the corrosion of a steel material buried in the soil is estimated from the measured particle size and color measurement value (estimation step). In the corrosion estimation, a corrosion rate is obtained from the measured particle size, a corrosion rate magnification is obtained from the measured color measurement value, a corrected corrosion rate is obtained by multiplying the corrosion rate by the corrosion rate magnification, and the corrosion of the steel material is estimated according to the obtained corrected corrosion rate.

Figure 2:
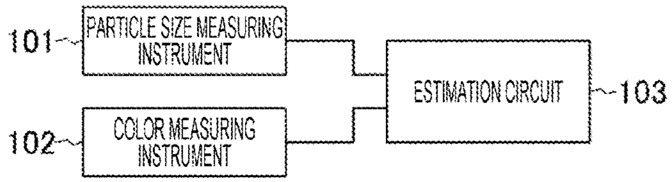
FIG. 2 is a configuration diagram illustrating a configuration of a corrosion estimation device according to an embodiment of the present invention.

Next, a corrosion estimation device for performing the above-described corrosion estimation method will be described with reference to FIG. 2. The corrosion estimation device includes a particle size measuring instrument 101 that measures the particle size of the soil, a color measuring instrument 102 that measures the color measurement value related to the color of the soil, and an estimation circuit 103 that estimates the corrosion of the steel material buried in the soil from the measured particle size and the measured color measurement value. The color measuring instrument 102 measures, for example, the color value as the color measurement value.

The estimation circuit 103 obtains the corrosion rate from the measured particle size, obtains the corrosion rate magnification from the measured color measurement value, obtains the corrected corrosion rate by multiplying the corrosion rate by the corrosion rate magnification, and estimates the corrosion of the steel material according to the obtained corrected corrosion rate. The estimation circuit 103 is a computer device provided with a central processing unit (CPU), a memory, and the like. The CPU operates (executes a program) by the program expanded in the memory, whereby the above-described function (estimation step) is realized. Furthermore, the estimation circuit 103 can also be configured by a programmable logic device (PLD) such as a field-programmable gate array (FPGA). The program for realizing the operation of the estimation step can be written in the FPGA by connecting a predetermined writing device.

As described above, since the soil corrosion is a complex system, how to extract and analyze a dominant factor related to the corrosion from a solid phase specific to a soil environment is a key for estimating the soil corrosion.

One piece of information of important solid phase is soil particle size. In the soil, a particle gap structure and particle packing density change depending on differences in particle size and particle size distribution, which greatly affects ease of oxygen supply from a soil surface layer and a wetted area of a metal surface by water captured by capillary action. The soil particle size is the most effective environmental factor for estimating information of a liquid phase and a gas phase that control presence or absence of corrosion occurrence for the soil corrosion.

As described above, information relating to the presence or absence of occurrence of soil corrosion can be obtained by the particle size of the soil, but the particle size of the soil alone is insufficient for estimating the soil corrosion. Even if climatic conditions such as temperature and humidity of places where facilities are installed are similar, for example, it is generally said that a corrosion progress rate is high in coastal areas and hot spring areas. Therefore, it is necessary to consider the presence or absence of chemical components in the environment that accelerates the corrosion progress while satisfying a corrosion occurrence condition.

The most important in estimating the chemical components in the soil is a color (soil color) of the soil. For example, a "soil group" classified by an agricultural land soil classification standard is classified by the soil color on the basis of the chemical components of the soil that are important for implementing agriculture. For example, kuroboku-tsuchi (in Japanese) (andosol) is black in color as the name implies and contains organic acids derived from humus. In addition, brown soil, yellow soil, and red soil are classified by the proportion of iron oxide in the soil, and gray soil exhibiting blue in color is also derived from reduced iron. From the above fact, it is possible to estimate an acceleration of corrosion from the chemical components in the soil on the basis of the soil color.

It is possible to measure the particle size of the soil as a factor for estimating the presence or absence of corrosion occurrence from the information of the solid phase and the liquid phase in the vicinity of the surface of the metal material buried in the soil, measure the soil color as a factor for estimating the chemical components that accelerate corrosion under the corrosion occurrence condition, and estimate a corrosion amount of the metal material buried in the ground from these measured two factors.

Figure 3:
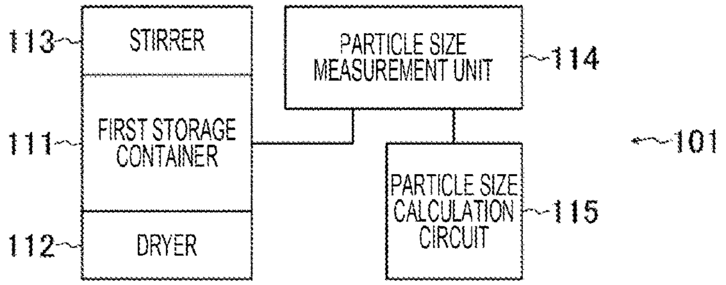
FIG. 3 is a configuration diagram illustrating a partial configuration of a corrosion estimation device according to an embodiment of the present invention.

Next, the corrosion estimation device will be described in more detail. First, the particle size measuring instrument 101 will be described with reference to FIG. 3. The particle size measuring instrument 101 includes a first storage container 111, a dryer 112, a stirrer 113, a particle size measurement unit 114, and a particle size calculation circuit 115. The particle size measuring instrument 101 performs a test for measuring the particle size of the soil.

In the particle size measuring instrument 101, first, the soil in which the steel material whose corrosion amount is to be estimated is buried is stored in the first storage container 111. The amount of the soil to be stored in the first storage container 111 varies depending on a particle size measurement method to be described below, but the maximum amount can be about 500 mL. The shape of the first storage container 111 is not limited as long as the first storage container 111 has a size capable of storing the amount of soil necessary for measurement.

The material constituting the first storage container 111 can be arbitrarily determined by a user. However, in a case where the first storage container 111 is made of a metal material, when wet soil is stored, a corrosion reaction occurs with the wet soil depending on the metal and the container is degraded, and further, a corrosion product is mixed in the wet soil, which may affect soil color measurement to be described below. Therefore, it is favorable to avoid the metal material in selection of the material constituting the first storage container 111.

In addition, in a case where drying of the soil in the first storage container 111 by the dryer 112 is performed by heating, it is favorable to avoid materials weak to heat. For example, the first storage container 111 can be made of a heat-resistant polymer resin, glass, or the like.

In a case where the soil stored in the first storage container 111 is in a wet state, a soil particle mass may be formed by a capillary phenomenon of water trapped in a particle gap. When the particle size measurement is performed in the presence of the soil particle mass, a large proportion of particles larger than an original particle size is detected, and it is difficult to obtain a true particle size. To prevent the above problem, it is important to remove the water in the particle gap, which is the cause of the soil particle mass, and the dryer 112 dries the soil in the first storage container 111.

For example, the dryer 112 dries the stored soil by applying heat to increase a temperature of the first storage container 111. Further, the dryer 112 can decompress an inside of the first storage container 111 and vacuum-dry the first storage container 111. Here, in the case of applying heat, it is necessary to select the material that the first storage container 111 can withstand up to the temperature set by the user.

In addition, in the case where the soil stored in the first storage container 111 contains humus and exhibits black, chemical components derived from organic substances are modified by heat, and not only properties inherent in the black soil are lost, but also a result obtained by the color measuring instrument 102 may be affected. Therefore, it is favorable to limit a temperature rise in the first storage container 111 to an upper limit of 50° C.

In addition, in the case of drying the soil stored in the first storage container 111 by decompression, it is important that the first storage container 111 is made of a material that can withstand decompression. For example, in the case of drying the soil by decompression, the first storage container 111 is favorably made of glass.

A drying operation in the dryer 112 is terminated when a water content of the soil stored in the first storage container 111 reaches 0%. For example, the soil water content of the first storage container 111 can be detected by installing a soil water content sensor in the first storage container 111. The dryer 112 is not limited to adopt the above-described drying method as long as the dryer has a mechanism that realizes a method capable of causing the soil water content in the first storage container 111 to reach 0%.

The stirrer 113 performs a stirring operation for the soil in the first storage container 111 having the soil water content of 0% by the drying of the dryer 112 in order to loosen the soil particle mass. The stirrer 113 is not limited as long as the stirrer has a mechanism capable of eliminating all the soil particle masses. For example, a mechanism that performs stirring with two rod-shaped stirring members in a circle can be used. Alternatively, a mechanism similar to an automatic stirrer employed in a food factory or the like can be employed.

The particle size measurement unit 114 measures the particle size of the soil in the first storage container 111 for which pretreatment of the soil has been performed by the dryer 112 and the stirrer 113. As the method of measuring the particle size, for example, JIS A 1204:2009 "The method for particle size distribution of soils" can be used. Further, the particle size can be measured conforming to JIS Z 8825: 2013 "Particle size analysis-Laser diffraction methods".

For example, in the case of performing the method for particle size distribution of soils, metal mesh sieves prescribed in JIS Z 8801-1 with mesh sizes of 75 mm, 53 mm, 37.5 mm, 26.5 mm, 19 mm, 9.5 mm, 4.75 mm, 2 mm, 850 μm, 425 μm, 250 μm, 106 μm, and 75 μm are prepared. The soil is put into the metal mesh sieve and sieved, and particle size distribution is calculated from a proportion of the soil particles left on each sieve.

In addition, with respect to the particle size of 75 μm or less, the particle size is calculated using a soil particle sedimentation method using a hydrometer. It is possible to calculate the particle size distribution by combining results of the sieving method for the soil particles of 75 μm or more and the sedimentation method for the soil particles of less than 75 μm. Note that, to perform the method for particle size distribution of soils, about 500 mL of soil is required to be stored in the first storage container 111.

In the particle size analysis-laser diffraction methods mentioned as another measurement technique capable of measuring the particle size, the soil particles are irradiated with laser light, diffracted/scattered light having different intensities depending on the size of the particles is generated, and a light intensity distribution pattern formed from the generated diffracted/scattered light is analyzed to calculate the particle size distribution.

The particle size measurement by the laser diffraction methods can be performed using a commercially available analytical instrument. Note that, to perform the particle size analysis-laser diffraction methods, the soil to be stored in the first storage container 111 can be about 50 mL. The soil used for the measurement by the particle size measurement unit 114 can be discarded as it is, and can also be reused in the color measuring instrument 102. In the case of discarding the soil, it is necessary to additionally prepare an amount of soil measurable by the color measuring instrument 102. Further, in the case of reusing the soil in the color measuring instrument 102, it is not necessary to prepare an additional amount of soil, but since the soil measured by the particle size measurement unit 114 is in a wet state, it is necessary to perform the drying operation by the dryer 112 and the removal of the soil mass by the stirrer 113 again.

The particle size measurement result measured by the particle size measurement unit 114 is sent to the particle size calculation circuit 115, and the particle size distribution is derived on the basis of the measurement result. The particle size distribution obtained by the particle size calculation circuit 115 is, for example, a graph in which a horizontal axis represents the particle size and a vertical axis represents frequency % or cumulative % of the frequency of each particle size.

Figure 4:
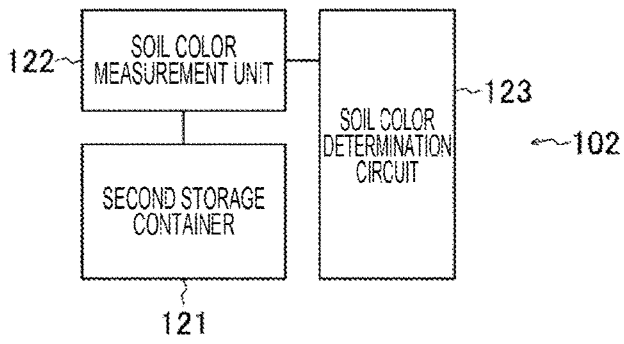
FIG. 4 is a configuration diagram illustrating a partial configuration of a corrosion estimation device according to an embodiment of the present invention.

Next, the color measuring instrument 102 will be described with reference to FIG. 4. The color measuring instrument 102 performs a test for measuring the color of the soil. First, the soil is transferred from the first storage container 111 of the particle size measuring instrument 101 to a second storage container 121. The shape, material, and the like of the second storage container 121 are not particularly limited as long as the soil color measurement can be performed. However, it is essential that the soil color is discriminative from the outside of the first storage container 111 regardless of either the case of using a measuring instrument or the case of visually confirming the soil color by a measurer is selected as a soil color measuring means, and thus it is favorable that an upper portion of the container is in a largely opened shape such as a petri dish or the entire surface of the container is made of a transparent material.

A soil color measurement unit 122 measures the soil color in the second storage container 121, and a soil color determination circuit 123 determines the measured soil color. For the soil color measurement in the soil color measurement unit 122, for example, a standard soil color chart in which standard soil colors are arranged by a Munsell system classification method can be used. In addition, a spectrophotometer can be used for the soil color measurement in the soil color measurement unit 122.

In the case of measuring the soil color using the standard soil color chart, it is favorable that the measurer who performs the measurement is always the same person in order to reduce a measurement error as much as possible when measuring the soil color pf a plurality of soils. The measurer who measures the soil color using the standard soil color chart completes the measurement by recording the color values of hue, brightness, and saturation described in the standard soil color chart. In the case of using the standard soil color chart for the soil color measurement, it is favorable to prepare at least about 20 mL of soil in the second storage container 121 in order to visually determine the soil color.

Next, the case of using the spectrophotometer for the soil measurement in the soil color measurement unit 122 will be described. The spectrophotometer is a type of photometer, and can obtain information regarding color by measuring wavelength intensity for each color. In the case of using the spectrophotometer as the soil color measurement unit 122, the second storage container 121 needs to be a transparent spectroscopic cell capable of measurement.

As described above, the color information stored by performing the measurement is sent to the soil color determination circuit 123 and converted as some color value. As the color value, for example, the CIE1976 (L*a*b*) color space (CIELAB) formulated by the International Commission on Illumination (CIE) can be used. In CIELAB, the color values are described as three coordinates of L* representing color brightness, a* representing red and green positions, and b* representing yellow and blue positions. The values of L*, a*, and b* can be calculated by the soil color determination circuit 123 and used as a soil color measurement result.

Next, the estimation circuit 103 will be described in detail. The estimation circuit 103 estimates the corrosion amount of the steel material buried in the measurement soil on the basis of the results obtained by the particle size measuring instrument 101 and the color measuring instrument 102. First, the particle size measurement result (particle size distribution) obtained by the particle size calculation circuit 115 and the soil color measurement result (soil color determination result) obtained by the soil color determination circuit 123 are sent to a memory of the estimation circuit 103. The estimation circuit 103 calculates and outputs a corrosion amount estimation result using each measurement result stored in the memory. Information regarding the corrosion rate by soil corrosion is acquired from the particle size measurement result (particle size distribution) obtained by the particle size calculation circuit 115 in the particle size measuring instrument 101.

As described above, the progress of the corrosion reaction is determined by the wetted area of the metal surface buried in the soil and an oxygen partial pressure. The wetted area depends on a capillary force of water trapped in the particle gap, which can be determined from a particle gap size, i.e. the particle size distribution.

Further, the same similarly applies to the oxygen partial pressure, after the particle gap is filled with water such as rain, the water penetrates deep into the ground and diffuses as gravitational water, and oxygen diffuses from the surface layer to the ground and supplied to the metal surface. The supplied oxygen can be dissolved in water and reach the metal surface as dissolved oxygen, but since a diffusion rate of the dissolved oxygen is $10^4$ times slower than the diffusion rate of gaseous oxygen, the oxygen required for the corrosion reaction is more likely to be supplied as the distance of diffusion in the soil as a gas is longer. That is, to increase the distance in which gaseous oxygen can be diffused, the water in the soil works in conjunction with a permeation diffusion rate, and the water permeation diffusion rate is also determined by the particle size distribution.

From the above facts, information regarding a temporal change in the corrosion rate can be obtained from the particle size distribution. As an example of the information regarding the temporal change in the corrosion rate, the temporal change in the corrosion rate estimated from results of measuring the particle size in the soil in various states is illustrated in FIG. 5.

Figure 5:
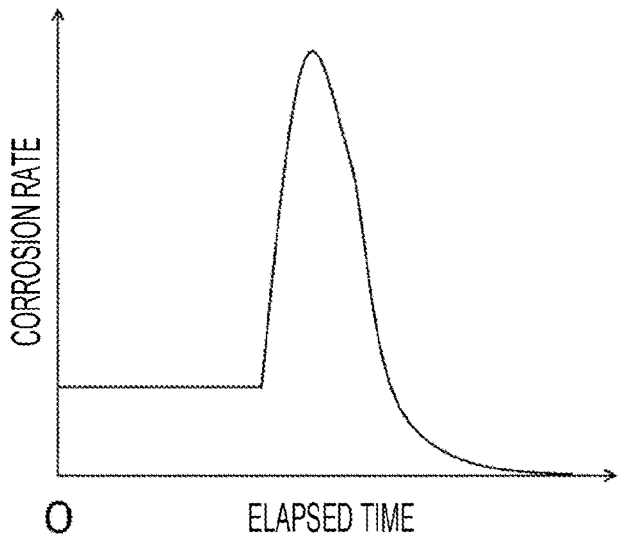
FIG. 5 is a characteristic chart illustrating a temporal change in a corrosion rate estimated from a particle size of soil.

In the graph illustrated in FIG. 5, a time point of an elapsed time 0 on the horizontal axis indicates a wet state in which all the soil particle gaps are filled with water, and the soil is dried as the water permeates and diffuses over time. As the drying progresses, the corrosion rate increases and reaches a maximum corrosion rate at some point. This is because oxygen becomes suppliable to a vicinity of the metal surface with the drying, and balance between water and oxygen necessary for the progress of the corrosion reaction is maintained. Further, after reaching the maximum corrosion rate, the corrosion rate is decreasing. This is because the drying has further progressed, and a sufficient amount of oxygen necessary for the corrosion reaction has been supplied, but the wetted area of the metal surface has been reduced.

The corrosion rate of the steel material buried in the ground exhibits a temporal change behavior as illustrated in FIG. 5, and the timing when the corrosion rate increases and the value of the maximum corrosion rate change depending on the particle size distribution. Therefore, a relationship between the particle size distribution and the temporal change behavior of the corrosion rate is examined in advance, the result is stored in the memory of the estimation circuit 103, and the stored result is compared with the result obtained by the particle size measuring instrument 101, so that the temporal change behavior of the corrosion rate can be easily obtained (extracted).

Note that the corrosion rate can be quantitatively measured using an electrochemical measurement method. Measurement by the electrochemical measurement method is repeatedly performed until the wet soil is dried, and the graph of FIG. 5 can be obtained in advance according to each particle size distribution. In addition, in a case where it is desired to save time and effort to acquire the temporal change behavior of the corrosion rate, only the maximum corrosion rate can be stored in the memory of the estimation circuit 103.

Figure 6:
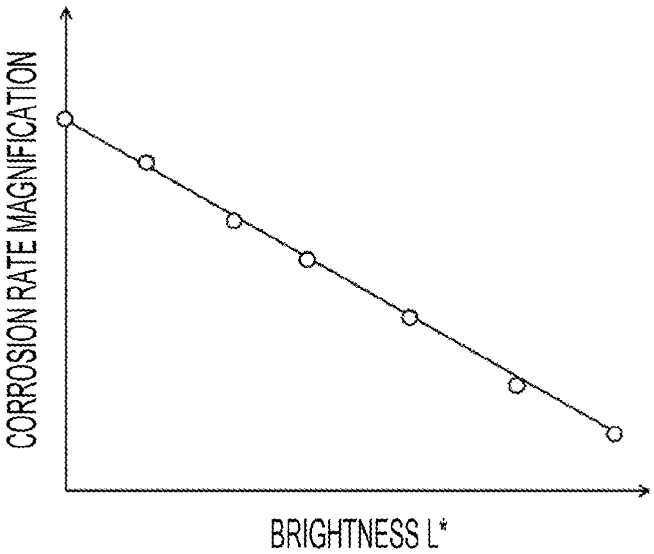
FIG. 6 is a characteristic chart illustrating a relationship between an L* value of CIELAB and a corrosion rate magnification.

Next, the estimation circuit 103 calculates the corrosion rate magnification from the result obtained by the color measuring instrument 102. FIG. 6 is a graph example illustrating a relationship between an L* value of CIELAB and a corrosion rate magnification. The L* value in CIELAB represents color brightness, and L*=0 indicates black and L*=100 indicates white diffuse color. Therefore, the closer to L*=0, the more organic acid derived from humus is contained in the soil.

Since an acid is a factor that accelerates corrosion, a true corrosion rate in each soil can be obtained by determining the corrosion rate magnification by the value of L* and multiplying (multiplying) the corrosion rate value in FIG. 5 by the corrosion rate magnification. Note that, as the relationship between the L* and the corrosion rate magnification, a graph in which the magnification is set higher as the L* is closer to 0 can be set, and also the relationship between the L* and the corrosion rate magnification can be examined in advance.

Figure 7:
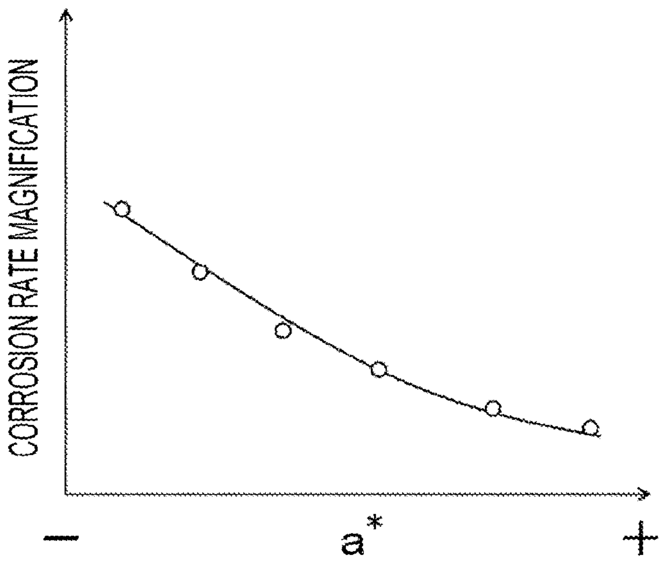
FIG. 7 is a characteristic chart illustrating a relationship between an a* value of CIELAB and a corrosion rate magnification.

FIG. 7 is a graph example illustrating a relationship between an a* value of CIELAB and the corrosion rate magnification. The a* value indicates red and green positions, and a negative a* value indicates green and a positive a* value indicates red. The soil exhibiting red in color contains a large amount of iron oxide. In the case where the amount of iron oxide generated as a corrosion product is large in the environment, it is considered that the corrosion reaction becomes slow and the corrosion rate ratio becomes low from the viewpoint of chemical equilibrium. Therefore, FIG. 7 can be set such that the corrosion rate magnification decreases in the case where the a* value takes a positive value, and the relationship between the a* value and the corrosion rate magnification can be examined in advance.

Figure 8:
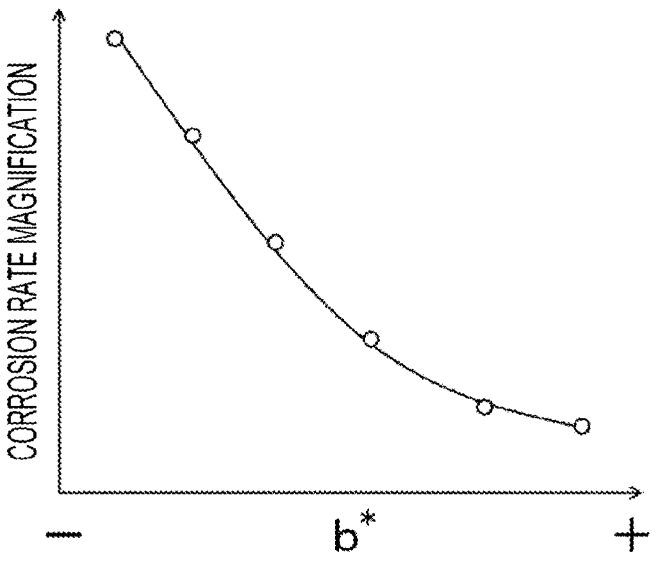
FIG. 8 is a characteristic chart illustrating a relationship between a b* value of CIELAB and a corrosion rate magnification.

FIG. 8 is a graph example illustrating a relationship between a b* value of CIELAB and a corrosion rate magnification. The b* value indicates yellow and blue positions, and a negative b* value indicates blue and a positive b* value indicates yellow. The soil exhibiting blue in color contains a large amount of reduced iron and has a characteristic that the corrosion rate remarkably increases because there are many receivers of electrons necessary for the progress of the corrosion reaction. Therefore, FIG. 8 can be set such that the corrosion rate magnification increases in the case where the b* value takes a negative value, and the relationship between the b* value and the corrosion rate magnification can be examined in advance.

The estimation circuit 103 calculates the corrected corrosion rate by multiplying the temporal change in the corrosion rate acquired from the result obtained by the particle size measuring instrument 101 or the maximum corrosion rate by the corrosion rate magnification acquired from the result obtained by the color measuring instrument 102. This calculation completes acquisition of all pieces of information regarding the corrosion rate. Next, the estimation circuit 103 performs estimation calculation of the corrosion amount from the information of the corrosion rate.

In the case where the temporal change in the corrosion rate is extracted from the result obtained by the particle size measuring instrument 101, the extracted temporal change indicates the temporal change in the corrosion rate from rainfall to the next rainfall, and thus it is possible to calculate the corrosion amount that progresses in one rain by integrating the extracted temporal change. Therefore, rainfall information of an area where the used soil was buried is acquired, and the corrosion amounts that progresses in one rain are added by the number of times of rains to obtain a corrosion amount R that progresses in one year.

In addition, in the case where the maximum corrosion rate is extracted by the particle size measuring instrument 101, the corrosion amount R that progresses in one year is similarly obtained from the maximum corrosion rate. A power law "$D=RT^n$ . . . (1)" known as an empirical model for predicting the corrosion progress from the required corrosion amount R may be used. D represents the corrosion amount [mm], T represents aging [year] of the buried metal material, and n represents a corrosion evaluation value of the material. Note that, since the value of n is empirically said to be 0.4 to 0.6, an intermediate value 0.5 of the value can be adopted. It is possible to estimate the corrosion amount of the buried metal material by introducing an aging value into T of the equation (1), the aging value describing how many years have elapsed since the buried metal material for which estimation of the corrosion amount is desired has been buried.

Figure 9:
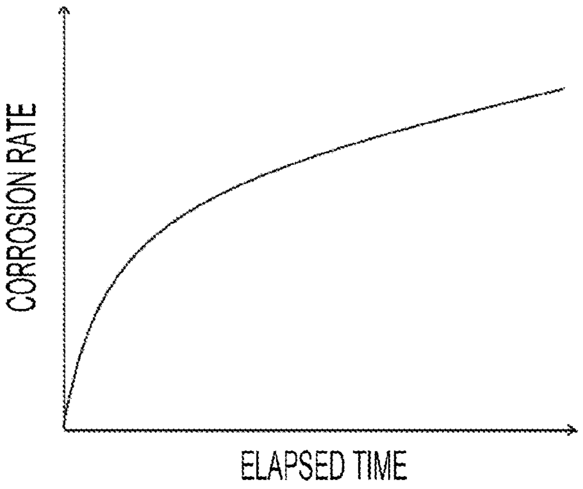
FIG. 9 is a characteristic chart illustrating a temporal change in a corrosion rate estimated from a particle size and color of soil.

FIG. 9 is a graph example illustrating the corrosion amount and the elapsed year estimated from the results of FIGS. 5, 6, 7, and 8, and is a graph example schematically illustrating the expression (1) that is an empirical model for predicting corrosion progress.

Figure 10:
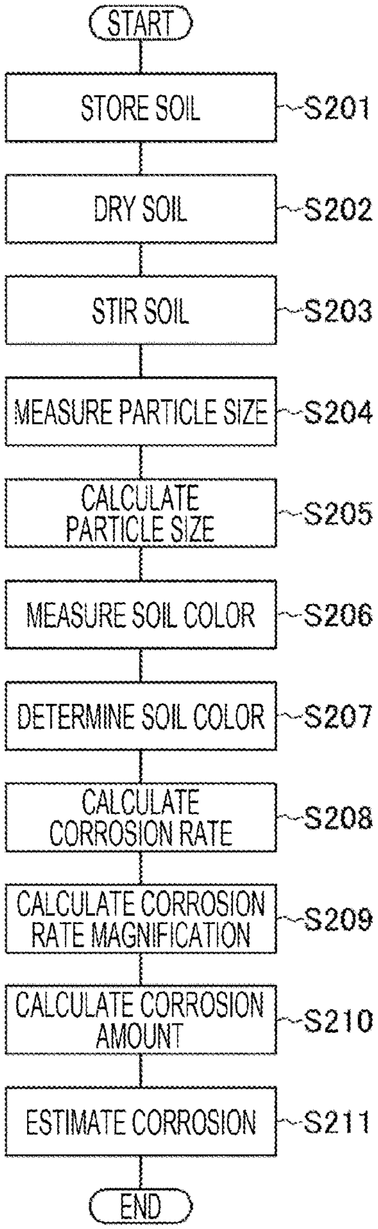
FIG. 10 is a flowchart for describing the corrosion estimation method according to the embodiment of the present invention in more detail.

Hereinafter, a more detailed corrosion estimation method will be described with reference to a flowchart of FIG. 10. First, in step S201, the soil is introduced into the corrosion estimation device, and the soil is stored in the first storage container 111 in the particle size measuring instrument 101. Next, in step S202, the dryer 112 is operated on the soil stored in the first storage container 111 to perform soil drying treatment. Next, in step S203, the stirrer 113 is operated on the soil for which the drying treatment has been performed to perform stirring treatment for removing the soil mass.

Next, in step S204, the particle size measurement unit 114 is operated to measure the particle size. Next, in step S205, the particle diameter distribution is obtained by the particle size calculation circuit 115 on the basis of the measured particle size. Next, in step S206, the soil color measurement unit 122 measures the color of the soil in the second storage container 121. Next, in step S207, the soil color determination circuit 123 determines the measured soil color.

Next, in step S208, the estimation circuit 103 calculates the corrosion rate of the steel material buried in the measurement soil on the basis of the result obtained by the particle size measuring instrument 101. Next, in step S209, the estimation circuit 103 calculates the corrosion rate magnification from the result obtained by the color measuring instrument 102. Next, in step S210, the estimation circuit 103 multiplies the corrosion rate value by the corrosion rate magnification to obtain a corrosion rate (corrected corrosion rate). Thereafter, in step S211, the estimation circuit 103 estimates corrosion (corrosion curve) of the metal material buried in the ground from the obtained corrosion rate.

As described above, according to embodiments of the present invention, since the corrosion of the steel material buried in the soil is estimated from the measured particle size and color measurement value, it becomes possible to easily estimate the corrosion of a metal material buried in the ground.

According to embodiments of the present invention, by estimating the soil corrosion only from the information of the solid phase in a short time with a small number of tests in the soil corrosion that is a complicated corrosion system, it becomes possible to easily perform the corrosion estimation at a low cost, it becomes possible to realize condition-based maintenance of a metal structure buried in the ground, and it is realized to ensure economy and safety associated with high efficiency.

Note that embodiments of the present invention is not limited to the embodiment described above, and it is obvious that many modifications and combinations can be made by those skilled in the art within the technical idea of embodiments of the present invention.

REFERENCE SIGNS LIST

101 Particle size measuring instrument
102 Color measuring instrument

103 Estimation circuit

The invention claimed is:

1. A corrosion estimation method comprising:

obtaining a sample of soil from a vicinity of a steel material buried in the soil;

storing the sample of soil in a storage container;

drying the sample of soil in the storage container;

a particle size measurement step of measuring a particle size of the sample of soil using laser diffraction;

a color measurement step of measuring a color measurement value related to a color of the sample of soil using a spectrophotometer; and an estimation step of estimating corrosion of the steel material based on the particle size measured in the particle size measurement step and the color measurement value measured in the color measurement step.

2. The corrosion estimation method according to claim 1, wherein the estimation step comprises:

obtaining a corrosion rate; and estimating the corrosion of the steel material based on the corrosion rate.

3. The corrosion estimation method according to claim 2, wherein the estimation step further comprises:

obtaining a corrosion rate magnification from the color measurement value; and obtaining a corrected corrosion rate based on the corrosion rate and the corrosion rate magnification, wherein estimating the corrosion of the steel material based on the corrosion rate comprises estimating the corrosion of the steel material based on the corrected corrosion rate.

4. The corrosion estimation method according to claim 3, wherein obtaining the corrected corrosion rate based on the corrosion rate and the corrosion rate magnification comprises multiplying the corrosion rate by the corrosion rate magnification.

5. The corrosion estimation method according to claim 1, wherein the color measurement step comprises measuring a color value as the color measurement value.

6. A corrosion estimation device comprising:

a particle size measuring instrument comprising a storage container, a dryer, and a particle size measurer, the storage container configured to store a sample of soil obtained from a vicinity of a steel material buried in the soil, the dryer configured to dry the sample of soil in the storage container, and the particle size measurer configured to measure a particle size of soil;

a color measuring instrument comprising a spectrophotometer, the spectrophotometer configured to measure a color measurement value related to a color of the sample of soil; and an estimation circuit comprising a processor and a memory, the memory storing a program that, when executed by the processor, causes the processor to estimate corrosion of the steel material based on the particle size and the color measurement value.

7. The corrosion estimation device according to claim 6, wherein the estimation circuit is configured to estimate the corrosion of the steel material by performing an estimation process comprising:

obtaining a corrosion rate; and estimating the corrosion of the steel material based on the corrosion rate.

8. The corrosion estimation device according to claim 7, wherein the estimation process further comprises:

obtaining a corrosion rate magnification from the color measurement value; and obtaining a corrected corrosion rate based on the corrosion rate and the corrosion rate magnification, wherein estimating the corrosion of the steel material based on the corrosion rate comprises estimating the corrosion of the steel material based on the corrected corrosion rate.

9. The corrosion estimation device according to claim 8, wherein obtaining the corrected corrosion rate based on the corrosion rate and the corrosion rate magnification comprises multiplying the corrosion rate by the corrosion rate magnification.

10. The corrosion estimation device according to claim 6, wherein the color measuring instrument is configured to measure a color value as the color measurement value.

11. A corrosion estimation method comprising:

obtaining a sample of soil from a vicinity of a steel material buried at a location;

storing the sample of soil in a storage container;

drying the sample of soil in the storage container;

measuring a particle size of the sample of soil using laser diffraction;

measuring a color measurement value related to a color of the sample of soil using a spectrophotometer; and estimating corrosion of the steel material based on the particle size and the color measurement value.

12. The corrosion estimation method according to claim 11, wherein estimating the corrosion of the steel material comprises:

obtaining a corrosion rate; and estimating the corrosion of the steel material based on the corrosion rate.

13. The corrosion estimation method according to claim 12, wherein estimating the corrosion of the steel material further comprises:

obtaining a corrosion rate magnification from the color measurement value; and obtaining a corrected corrosion rate based on the corrosion rate and the corrosion rate magnification, wherein estimating the corrosion of the steel material based on the corrosion rate comprises estimating the corrosion of the steel material based on the corrected corrosion rate.

14. The corrosion estimation method according to claim 13, wherein obtaining the corrected corrosion rate based on the corrosion rate and the corrosion rate magnification comprises multiplying the corrosion rate by the corrosion rate magnification.

15. The corrosion estimation method according to claim 11, wherein measuring the color measurement value comprises measuring a color value of the sample of soil as the color measurement value.

16. The corrosion estimation method according to claim 11 further comprising stirring the sample of soil after drying the sample of soil.

17. The corrosion estimation method according to claim 11, wherein drying the sample of soil comprises applying heat to the sample of soil.

18. The corrosion estimation method according to claim 11, wherein drying the sample of soil comprises vacuum-drying the sample of soil.

* * * * *